United States Patent [19]
Freidel

[11] Patent Number: 5,970,212
[45] Date of Patent: Oct. 19, 1999

[54] WATERLESS VAPORIZER

[76] Inventor: Alan I. Freidel, 7231 SW. 146th Ter., Miami, Fla. 33158

[21] Appl. No.: 09/188,742

[22] Filed: Nov. 9, 1998

[51] Int. Cl.[6] .................................. H05B 3/14; F22B 1/28
[52] U.S. Cl. .......................... 392/405; 392/386; 392/390; 392/394; 392/395; 392/403; 392/405
[58] Field of Search ....................... 392/386, 390, 392/391, 394, 395, 403, 405, 406; 219/520, 521, 536, 538, 544, 546; 239/44, 45

[56] References Cited

U.S. PATENT DOCUMENTS

| | | | |
|---|---|---|---|
| 3,872,280 | 3/1975 | Van Dalen | 392/390 |
| 4,571,485 | 2/1986 | Spector | 392/395 |
| 4,731,520 | 3/1988 | Glucksman et al. | 392/390 |
| 4,853,517 | 8/1989 | Bowen et al. | 392/390 |

OTHER PUBLICATIONS

Instruction brochure of Juvenile Products Corp. For "Mountain Breeze" Vaporizer; (prior to 1977).

Primary Examiner—Philip H. Leung
Assistant Examiner—Fadi H. Dahbour
Attorney, Agent, or Firm—Baker & Botts, L.L.P.

[57] ABSTRACT

A waterless vaporizer has a casing containing a heating module that causes vapors to be emitted from a refill pad that is impregnated with menthol and eucalyptus oil by slightly heating the pad and producing a thermally induced convective air flow through the pad. A top member of a casing has a planar pad-receiving surface with holes in it on which the pad can be placed in any selected position between a "low" output and a "high" output position on the surface. A pivotable and vertically displaceable chimney member fits over the pad. The chimney member has a pad retainer/holder portion, the top wall of which provides an alternative position for the pad. A power switch and an indicator lamp facilitate use of the vaporizer. All electrical components are highly durable and fully insulated. The vaporizer is assembled without any screws or equivalent fasteners.

20 Claims, 3 Drawing Sheets

WATERLESS VAPORIZER

BACKGROUND OF THE INVENTION

Juvenile Products Corp. of Miami, Fla. which holds license rights in the present invention, marketed a waterless vaporizer in the United States under the trademark "MOUNTAIN BREEZE" for several years. Production of the "MOUNTAIN BREEZE" vaporizer, which was made in England, was discontinued in 1996.

The "MOUNTAIN BREEZE" vaporizer had a case containing two small electrical resistors of the type used in electronic circuits that thermally induced an air flow through openings in the case and through a refill pad supported on a pad-supporting grille on the top of the case. The pad was impregnated with menthol dissolved in eucalyptus oil, and the thermally induced air flow vaporized the menthol and conducted it into the environment. The pad-receiving grille surface was large enough to permit the pad to be placed in a selected position between a "low" and a "high" position on the surface. A pivotable and vertically displaceable chimney fit over the pad and upon pivoting by the user moved the pad with it. Outlet holes in the chimney released the vapors to the environment.

Various aspects of the design and construction of the "MOUNTAIN BREEZE" vaporizer were detrimental to its durability and ease of use and may have played a role in its disappearance from the market place. For example, there was no power switch—the unit was simply plugged into an outlet. The resistors were mounted on a circuit board and connected to the power cord by soldered connections, which were prone to sparking and failure.

SUMMARY OF THE INVENTION

An object of the present invention is to provide a waterless vaporizer that is constructed to be significantly more durable and more convenient to use than the "MOUNTAIN BREEZE" product was. It is also an object to improve various aspects of the performance and to enhance the versatility of a waterless vaporizer, especially with regard to variations in the vapor output. Yet another object is to facilitate assembly of a waterless vaporizer, thereby reducing manufacturing costs.

The foregoing objects are attained, in accordance with the present invention, by a waterless vaporizer that includes a case having a bottom member and a top member defining a closed receptacle. The top member has an arcuate planar pad-receiving surface that is adapted to receive a refill pad in any of a plurality of selected positions. A chimney member is mounted on the top member of the case for pivotal movement about an axis and for displacement along the axis so that it can be lifted up to enable a refill pad to be placed on the pad-receiving surface of the top member of the case. Air inlet openings in the bottom member of the case and air outlet openings in the pad-receiving surface allow air to flow through the receptacle and through a refill pad on the pad-receiving surface of the top member of the case.

As described so far, the waterless vaporizer is similar to the "MOUNTAIN BREEZE" vaporizer. The present invention incorporates several significant improvements. One of the improvements is that the chimney member has an open-bottomed box-like refill pad retainer/holder portion overlying a portion of the pad-receiving surface of the top member. The pad retainer/holder portion has an upper surface on which a refill pad can be placed, thereby making it unnecessary for the user to lift up the chimney member and place the refill pad under the chimney member on the pad-receiving surface of the top member of the case. Some infirm users find it difficult to manipulate the chimney member and will benefit from being able to place the pad on the upper surface of the retainer/holder portion of the chimney member. Moreover, a refill pad placed on the chimney member is less highly heated than a pad placed on the pad-receiving surface of the top member of the case, thus reducing the rate of evolution of vapor from the pad. The pad will last longer, and in some instances the reduced rate of vapor evaporation is more suitable for the environment or the user's desire than the rates that occur when the pad is positioned on the pad-receiving surface of the top member of the case. The chimney member may have a knob to facilitate rotating it.

Another improvement is the provision of an elongated heating module, which has an electrical resistance wire fully encapsulated in a high temperature-resistant, heat-conducting polymeric material. The heating module is received in the receptacle below a portion of the pad-receiving surface of the top member adjacent one of the side edges thereof so as to establish a gradient of heat and air flow in the circumferential direction along the pad-receiving surface. The heating module above is highly durable, resistant to corrosion and functions more effectively than the resistors of the "MOUNTAIN BREEZE" vaporizer by providing more uniform heat output. It is advantageous for the molded member of the heating module to include a mounting lug having a pair of mounting holes to enable it to be attached to the case by reception of mounting bosses with an interference fit in the mounting holes of the mounting lug. That feature greatly facilitates installation of the heating module in the case.

The convenience of use of a waterless vaporizer, according to the present invention, is enhanced by providing an indicator lamp on the case that lights up when the heating module is energized. The vapor emitted by the vaporizer is invisible, so a user will not know whether the vaporizer is on or off by observation, absent a lamp. The indicator lamp also serves as a night light and a "locator" for the vaporizer. Preferably, the indicator lamp is received entirely within the enclosure proximate to the pad-receiving surface so that light from the lamp is emitted through the openings in the pad-receiving surface of the top member of the case and the openings in the top wall of the pad retainer/holder portion of the chimney member. Installation of the lamp entirely within the case protects it from being broken and facilities installation. In particular, the bottom member of the case may include a lamp holder cavity defined by a perimeter wall portion of the bottom member and a rib adjacent the wall portion. The lamp is received in the lamp holder cavity, and a dependent lug on the top member of the case retains the lamp in the lamp holder cavity. Advantageously, the lamp is an A1C neon lamp and has wire leads that are fully insulated by a tubular sheathe.

A waterless vaporizer according to a preferred embodiment has a power cord connected to the resistance wire of the heating module by tabs on the module and fully insulated crimp-on receptacles on the power cord. That manner of connection is highly durable and facilitates assembly, in contrast with soldered connections. Convenience of use is greatly improved by providing a switch, such as a thumb wheel operated switch, in the power cord and remote from the case.

DESCRIPTION OF THE DRAWINGS

For a more complete understanding of the present invention, and the advantages thereof, reference may be made to the following written description of an exemplary embodiment, taken in conjunction with the accompanying drawings.

DESCRIPTION OF THE EMBODIMENT

Figure 1:
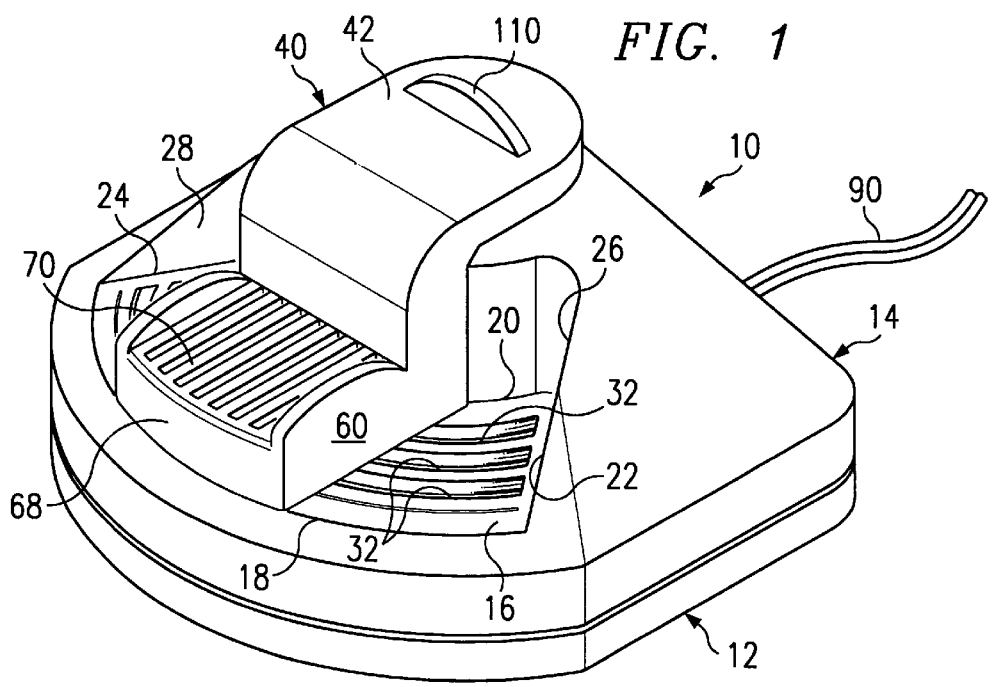
FIG. 1 is a three-quarter front pictorial view of the embodiment, which is also taken from a vantage point above.

A case 10 is composed of a generally cup-shaped bottom member 12 and a generally dome-shaped top member 14, which fit together along mating peripheral flanges and define a closed receptacle. The top and bottom members 12 and 14 are joined by bosses that are in a telescopic interference fit. Each of the members 12 and 14 is molded from a durable polymeric material, such as PVC. The top member 14 has an arcuate planar pad-receiving surface 16 that is defined by radially spaced-apart, arcuate front and rear edges 18 and 20, which have a common center axis, and side edges 22 and 24. The surface 16 is bordered by planar side wall portions 26 and 28 and a circular cylindrical wall portion 30, the axis of which coincides with the center axis of the arcuate edges 18 and 20. The pad-receiving surface 16 is constituted by the upper edges of a grille that has radial ribs and sloping arcuate ribs, which define arcuate openings or slots 32 in the surface 16.

Figure 6:
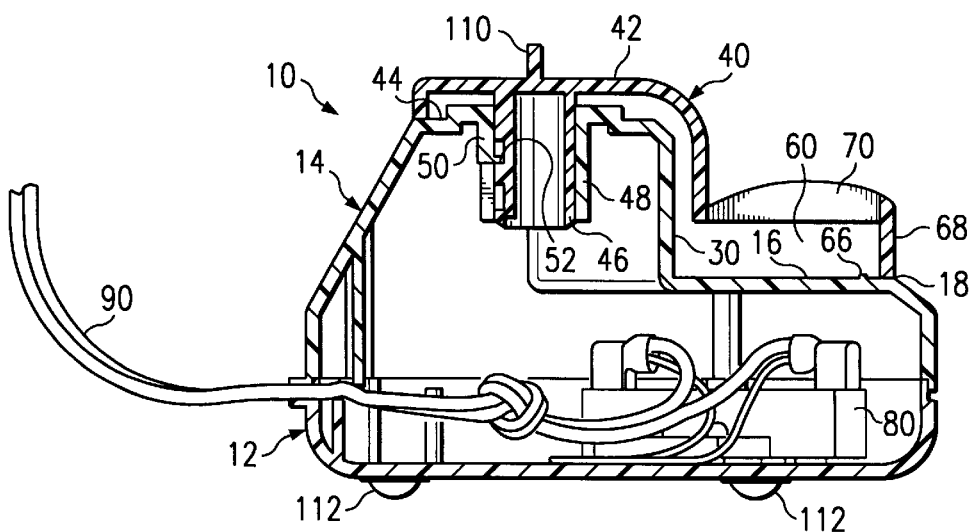
FIG. 6 is a side cross-sectional view taken along the lines 6—6 of FIG. 2.

A chimney member 40 is mounted on the top member 14 of the case 10 for pivotal movement about the center axis of the surface 16 and for displacement along the center axis. A top arm portion 42 of the chimney member 40 overlies a flat wall portion 44 on the top of the top member 14 of the case and has a dependent circular cylindrical tubular boss 46 that is telescopically received with a sliding fit within a tubular circular cylindrical boss 48 that depends from the wall portion 44 (see FIG. 6). A snap-fit tongue 50 on the top member 14 protrudes through a slot in the boss 48 and into a slot in the boss 46 and allows the chimney member to be pressed into place on the top member and retained by engagement of the tongue 50 with a shoulder 52 on the boss 46 that is constituted by the lower edge of the slot in the boss 46. The slot in the boss 46 extends circumferentially through an arc sufficient to permit the chimney member 40 to rotate in the manner described below.

The chimney member 40 has side walls 60 and 62, each of which has a rear edge that is in sliding clearance with the cylindrical surface 30 of the top member 14 and a bottom edge that, when the chimney member is in a lower position on the top member 14, engages a shallow rib 66 adjacent the outer edge 18 of the pad-receiving surface 16 and is in close clearance with the pad-receiving surface 16. An arcuate front wall 68 and a top wall 70 of the chimney member 40 define with the side walls 60 and 62 an open-bottomed box-like pad retainer/holder portion of the chimney member 40. The top wall 70 is constituted by a grille that defines air flow outlet openings from the downwardly-opening cavity formed by the pad retainer/holder portion of the chimney member.

Figure 5:
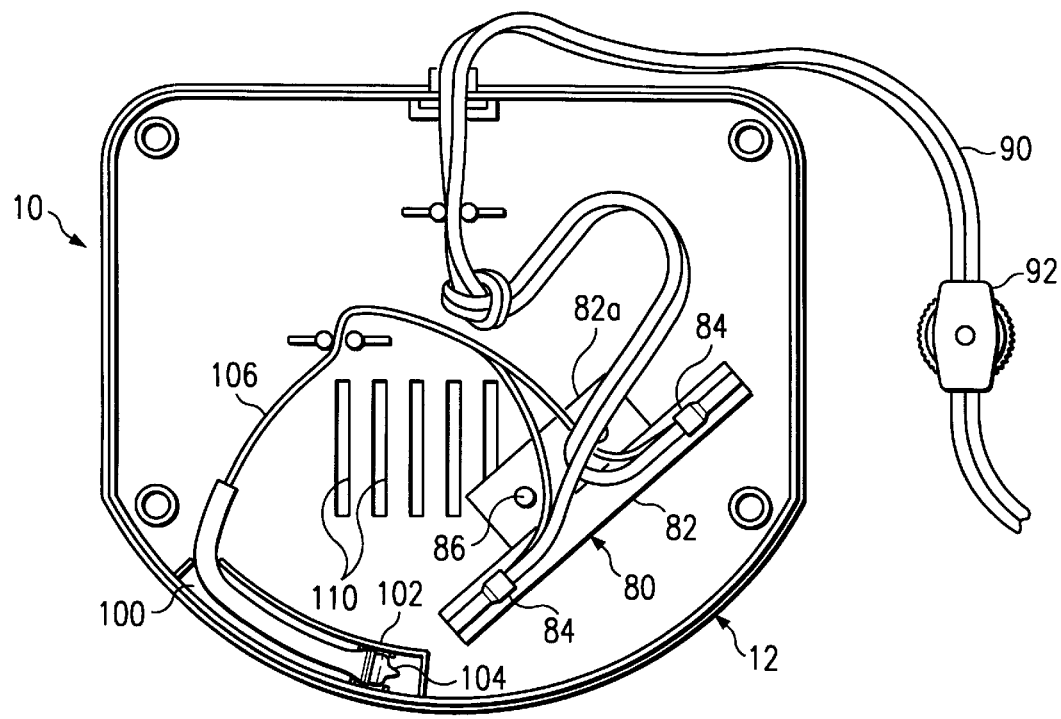
FIG. 5 is a top plan view with the top member of the case removed.

An elongated heating module 80 (see FIG. 5) is mounted on the bottom member 12 of the case 10 in a position such that it is located eccentrically in the circumferential direction with respect to the center of the pad-receiving surface 16 of the top member and thus adjacent one of the side edges (i.e., edge 22) of the surface 16. The module 80 has a resistance wire (not shown) that is completely encapsulated in a molded body 82 of a high temperature-resistant, heat-conducting polymeric material and is connected to a pair of electrical terminal tabs (not shown), each of which receives a fully insulated flag-type receptacle 84. The molded body 82 of the heating module has a laterally extending mounting flange 82a. Holes in the mounting flange accept mounting pins 86 that project up from the base with an interference fit. Spacer bosses (not shown) on the bottom member 12 support the heating module in clearance from the bottom wall to minimize heat transfer from the module to the bottom member. The heating module draws about three watts at 120 volts.

One conductor wire of a two conductor cord set 90 is received in a funnel entry and crimp area of the post of each receptacle 84. The cord is knotted for retention in the case and captured by bosses on the case. A thumb-wheel switch 92 is interposed in the cord at a suitable distance from the case. Note that the fully insulated receptacles 84 eliminate exposed wiring for added safety, even though the wiring and heating module are enclosed in and protected by the case 10.

The bottom member 12 of the case has an upwardly open lamp holder cavity 100, which is located adjacent the front of the case 10 and is defined by a portion of the side flange of the bottom member 12 and a rib 102. A standard type A1C neon lamp 104 is received in the cavity 100 and is connected by wires 106 to the receptacles 84. A length of PVC tubing 108 covers the wire leads of the lamp—again, additional safety is provided by fully insulating the wiring for the lamp.

The vaporizer is used with a pad of an air permeable, absorbent material that is initially saturated with menthol dissolved in eucalyptus oil. At the option of the user the pad is either placed on the pad-receiving surface 16 of the case 10 under the chimney member or on the top wall 70 of the retainer/holder portion of the chimney member 40. In the former case the user lifts up the chimney member, slides the pad under the retainer/holder portion, and then moves the chimney member back down. In either case, the user may rotate the chimney member to any desired location circumferentially along the surface 16. A knob 110 on the top arm of the chimney member facilitates rotating the chimney member.

Figure 2:
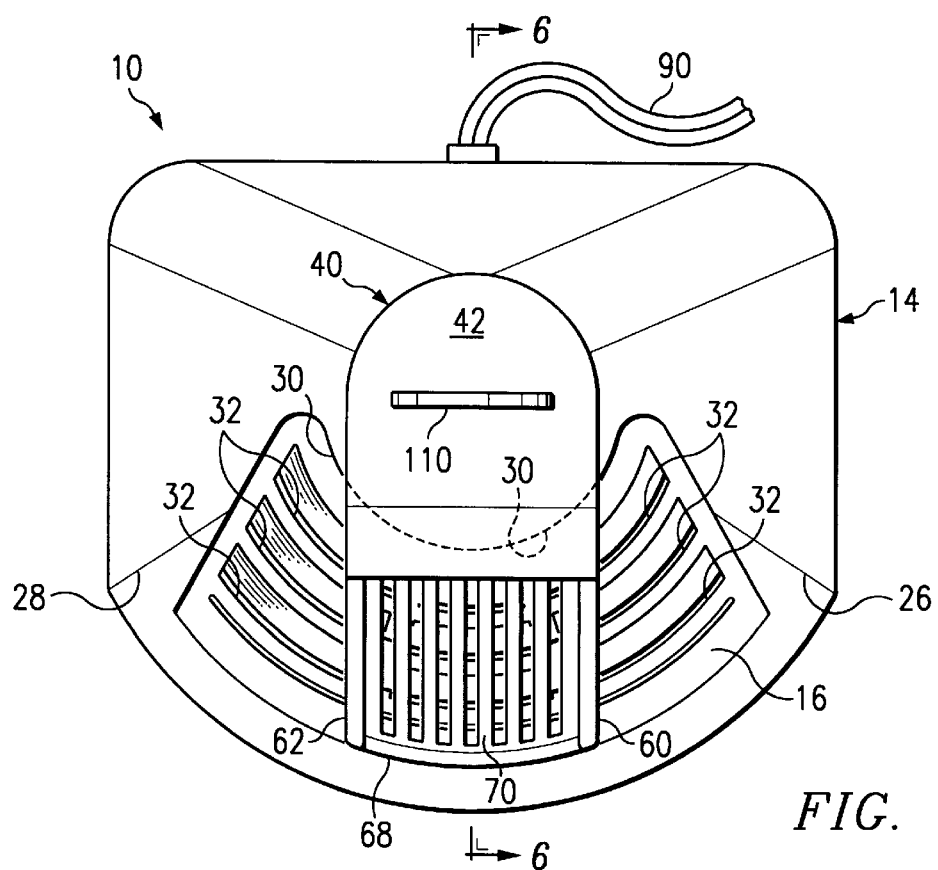
FIG. 2 is top plan view of the embodiment.
Figure 3:
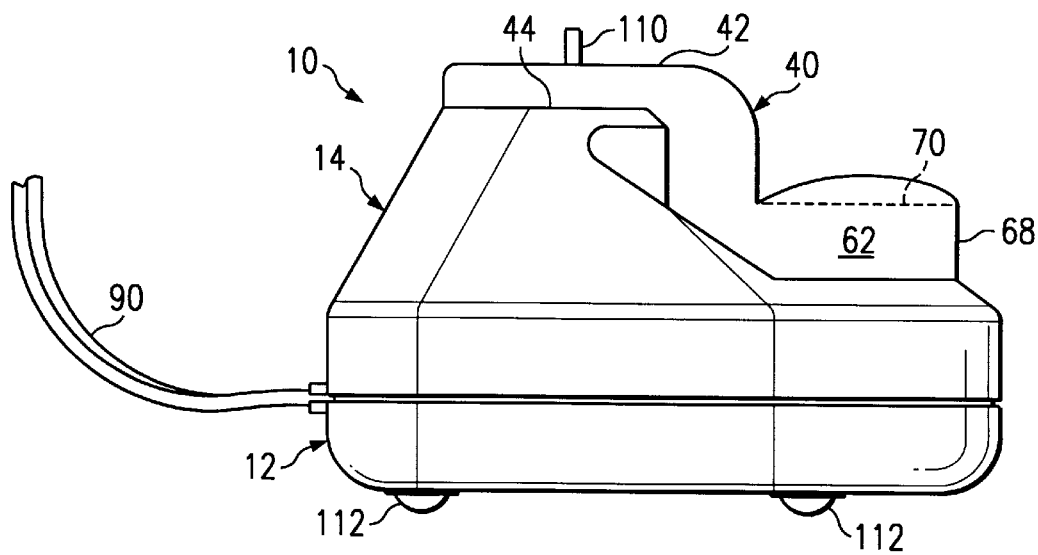
FIG. 3 is a left side elevational view and is also a mirror image of the right side.
Figure 4:
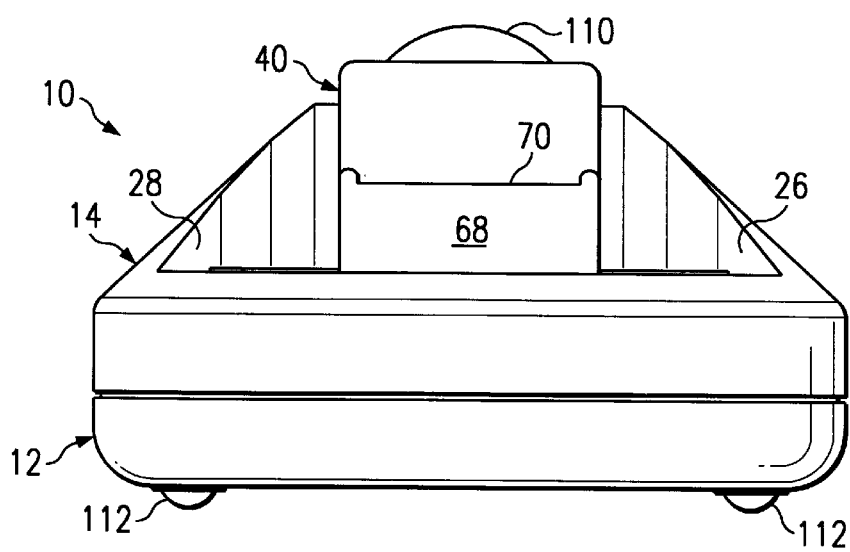
FIG. 4 is a front elevational view.

When the vaporizer is turned on by cycling the switch 92, the lamp 104 is illuminated, thus indicating to the user that the vaporizer is operating. The heating module 80 heats up, thus heating the air within the case and also heating a portion of the case proximate to it, but only to a small extent—the part of the case immediately above the heating module is warm to the touch but not enough to cause discomfort when the hand is held against it. The heat induces a flow of air, which is taken into the interior of the case through inlet holes 110 (see FIG. 5) located in the bottom wall of the bottom member of the case below the pad-receiving surface 16. The case rests on soft, non-slip pads 112, thus leaving space between the bottom of the case and a surface on which the vaporizer rests for air to flow to the inlet holes 110. The air is expelled through the holes of the grille that forms the pad-receiving surface 16. The air flow is strongest immediately above the heating module and weakest at the end of the pad-receiving surface 16 farthest from the heating module. By moving the chimney member so that it lies above the heating module (to the right in FIG. 2) the air flow is greatest and the refill pad is also heated relatively highly. The combination of heat and air flow vaporize the menthol and conduct it into the environment at a relatively high rate. When the chimney member 40 is positioned at the far left end of the surface 16, there is little heat and a low air flow rate, and the rate of vaporization of the menthol and convective flow of the vapor into the environment is significantly lower than at the "high" end of the surface. The user may select any desired position of the chimney member, depending on his or her desire in terms of the intensity of the vapor he or she wants to inhale.

The indicator lamp 104 provides a night light and a "locator" for the vaporizer in a dark room. The light from the lamp shines through the holes in the surfaces 16 and 70 and reflects from surfaces of the case and the chimney member upon which it impinges. The illumination enables the user to locate and adjust the vaporizer or replace a spent pad in a dark room.

What is claimed is:

1. A waterless vaporizer comprising
    a case having a bottom member and a top member defining a closed receptacle,
        the top member having an arcuate planar pad-receiving surface adapted to receive a refill pad in any of a plurality of selected positions between side edges thereof,
    a chimney member mounted on the top member of the case for pivotal movement about a center axis and for displacement along the center axis so that it is adapted to be lifted up to enable a refill pad to be placed on the pad-receiving surface of the top member of the case,
        the chimney member having an open-bottomed box-like refill pad retainer/holder portion overlying a portion of the pad-receiving surface of the top member, the pad retainer/holder portion being both a retainer and a holder for a refill pad and being adapted to cover a refill pad received on the pad-receiving surface of the top member of the case, and
        the pad retainer/holder portion having a top wall adapted to receive a refill pad on the upper surface thereof at the option of a user in lieu of positioning a refill pad under the pad retainer/holder portion on the pad-receiving surface of the top member of the case; air inlet openings in the bottom member of the case, air outlet openings in the pad-receiving surface, and air outlet openings in the top wall of the refill pad retainer/holder portion of the chimney member, all said openings defining a path for convective air flow through the receptacle and the pad retainer/holder portion of the chimney member; and
    an elongated heating module having an electrical resistance wire fully encapsulated in a molded member of a high temperature-resistant, heat-conducting polymeric material and received in the receptacle below a portion of the pad-receiving surface of the top member adjacent one of the side edges thereof so as to establish a gradient of heat and thermally induced air flow along the pad-receiving surface in a circumferential direction.

2. The waterless vaporizer according to claim 1 and further comprising an indicator lamp associated with the case and energized when the heating module is energized to emit light that is visible to a user.

3. The waterless vaporizer according to claim 2 wherein the lamp is received entirely within the enclosure proximate to the pad-receiving surface so that light from the lamp is emitted through the openings in the pad-receiving surface of the top member of the case and the openings in the top wall of the pad retainer/holder portion of the chimney member.

4. The waterless vaporizer according to claim 3 wherein the bottom member of the case includes a lamp holder cavity defined by a perimeter wall portion of the bottom member and a rib adjacent the wall portion, the lamp is received in the lamp holder cavity, and a dependent lug on the top member of the case retains the lamp in the lamp holder cavity.

5. The waterless vaporizer according to claim 4 and further comprising a power cord connected to the resistance wire of the heating module by tabs on the module and fully insulated crimp-on receptacles on the power cord and wherein the lamp includes leads that are crimped to the crimp-on receptacles.

6. The waterless vaporizer according to claim 3 wherein the lamp is an A1C neon lamp and has leads fully insulated by a tubular sheathe.

7. The waterless vaporizer according to claim 1 and further comprising a power cord connected to the resistance wire of the heating module by tabs on the module and fully insulated crimp-on receptacles on the power cord.

8. The waterless vaporizer according to claim 1 and further comprising a power cord connected to the resistance wire of the heating module and a switch in the power cord and remote from the case.

9. The waterless vaporizer according to claim 1 wherein the chimney member further includes a knob to facilitate rotating it.

10. The waterless vaporizer according to claim 1 wherein the molded member of the heating module includes a mounting lug having a pair of mounting holes and the case includes mounting bosses received with an interference fit in the mounting holes of the mounting lug.

11. A waterless vaporizer comprising
    a case having a bottom member and a top member defining a closed receptacle,
        the top member having an arcuate planar pad-receiving surface adapted to receive a refill pad in any of a plurality of selected positions, said pad-receiving surface being defined by spaced-apart inner and outer arcuate edges having a common center axis and by angularly spaced-apart lateral edges, and
        the top member having a dome portion adjacent the pad-receiving surface that includes a circular cylindrical front surface having its center coincident with the center axis;
    a chimney member mounted on the top member of the case for pivotal movement about the center axis and for displacement along the center axis so that it is adapted to be lifted up to enable a refill pad to be placed on the pad-receiving surface of the top member of the case,
        the chimney member having a box-like refill pad retainer/holder portion overlying a portion of the pad-receiving surface of the top member, the pad retainer/holder portion being both a retainer and a holder for a refill pad, the pad retainer/holder portion having spaced-apart side walls that are in sliding clearance with the pad-receiving surface when the chimney member is in a lower position and are in sliding clearance with the cylindrical front surface of the dome portion of the top member, a front wall in sliding clearance with the pad-receiving surface adjacent the front edge thereof when the chimney member is the lower position, and a top wall adapted to receive a refill pad at the option of a user in lieu of positioning a refill pad on the pad-receiving surface of the top member of the case;
    air inlet openings in the bottom member of the case in a position generally below a medial portion of the pad-receiving surface of the top member, air outlet openings in the pad-receiving surface, and air outlet openings in the top wall of the refill pad retainer/holder portion of the chimney member, all said openings defining a path for convective air flow through the receptacle and the pad retainer/holder portion of the chimney member; and an elongated heating module having an electrical resistance wire fully encapsulated in a molded member of a high-temperature resistant, heat-conducting polymeric material and received in the receptacle below a portion of the pad-receiving surface of the top member adjacent one of the side edges thereof so as to establish a gradient of heat and thermally induced air flow along the pad-receiving surface in the circumferential direction.

12. The waterless vaporizer according to claim 11 and further comprising an indicator lamp associated with the case and energized when the heating module is energized to emit light that is visible to a user.

13. The waterless vaporizer according to claim 12 wherein the lamp is received entirely within the enclosure proximate to the pad-receiving surface so that light from the lamp is emitted through the openings in the pad-receiving surface of the top member of the case and the openings in the top wall of the pad retainer/holder portion of the chimney member.

14. The waterless vaporizer according to claim 13 wherein the bottom member of the case includes a lamp holder cavity defined by a perimeter wall portion of the bottom member and a rib adjacent the wall portion, the lamp is received in the lamp holder cavity, and a dependent lug on the top member of the case retains the lamp in the lamp holder cavity.

15. The waterless vaporizer according to claim 14 and further comprising a power cord connected to the resistance wire of the heating module by tabs on the module and fully insulated crimp-on receptacles on the power cord and wherein the lamp includes leads that are crimped to the crimp-on receptacles.

16. The waterless vaporizer according to claim 13 wherein the lamp is an A1C neon lamp and has leads fully insulated by a tubular sheathe.

17. The waterless vaporizer according to claim 11 and further comprising a power cord connected to the resistance wire of the heating module by tabs on the module and fully insulated crimp-on receptacles on the power cord.

18. The waterless vaporizer according to claim 11 and further comprising a power cord connected to the resistance wire of the heating module and a switch in the power cord and remote from the case.

19. The waterless vaporizer according to claim 11 wherein the chimney member further includes a knob to facilitate rotating it.

20. The waterless vaporizer according to claim 11 wherein the molded member of the heating module includes a mounting lug having a pair of mounting holes and the case includes mounting bosses received with an interference fit in the mounting holes of the mounting lug.

* * * * *